United States Patent [19]

Rody

[11] 4,340,533
[45] Jul. 20, 1982

[54] NOVEL STABILIZERS

[75] Inventor: Jean Rody, Riehen, Switzerland

[73] Assignee: Ciba-Geigy Corporation, Ardsley, N.Y.

[21] Appl. No.: 191,721

[22] Filed: Sep. 29, 1980

Related U.S. Application Data

[63] Continuation of Ser. No. 50,572, Jun. 21, 1979, abandoned.

[30] Foreign Application Priority Data

Jul. 3, 1978 [GB] United Kingdom ............... 28653/78

[51] Int. Cl.$^3$ ...................... C07D 211/50; C08K 5/34
[52] U.S. Cl. ..................................... 524/99; 546/222
[58] Field of Search ................. 260/45.8 NP; 546/222

[56] References Cited

U.S. PATENT DOCUMENTS

| | | | |
|---|---|---|---|
| 3,285,855 | 11/1966 | Dexter et al. | 260/45.85 B |
| 3,992,390 | 11/1976 | Holt et al. | 260/45.8 NP |
| 4,075,165 | 2/1978 | Soma et al. | 260/45.8 NP |
| 4,148,784 | 4/1979 | Malherbe et al. | 260/45.8 NP |
| 4,197,236 | 4/1980 | Rosenberger et al. | 546/222 |

Primary Examiner—John Kight, III
Assistant Examiner—R. A. White
Attorney, Agent, or Firm—Harry Falber

[57] ABSTRACT

2,2,6,6-Tetramethylpiperidine derivatives of the formula:

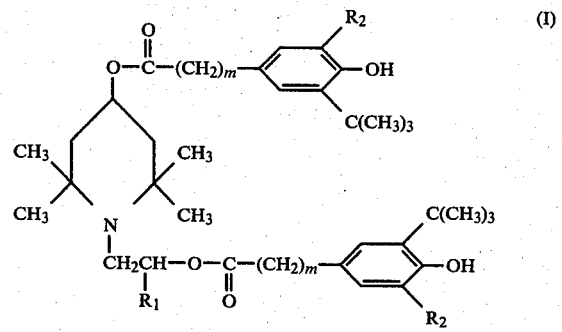

wherein m is 0, 1 or 2, $R_1$ is hydrogen, methyl, ethyl, phenoxymethyl or phenyl and $R_2$ is $C_1$–$C_8$ alkyl, are excellent stabilizers for synthetic polymers.

3 Claims, No Drawings

NOVEL STABILIZERS

This is a continuation of application Ser. No. 50,572, filed on June 21, 1979, now abandoned.

The invention relates to novel 2,2,6,6-tetramethyl-piperidine derivatives and synthetic polymer compositions stabilized by adding therein said derivatives.

Heretofore, there are disclosed in U.S. Pat. No. 3,992,390 2,2,6,6-tetramethylpiperidine derivatives containing a 3,5-di-tert.-butyl-4-hydroxyphenyl group in the molecule, such as 4-(3,5-di-tert.-butyl-4-hydroxy-benzoyloxy)-2,2,6,6-tetramethylpiperidine and 4-[3-(3,5-di-tert.-butyl-4-hydroxy-phenyl)-propionyloxy]-2,2,6,6-tetramethyl-piperidine, as stabilizers for synthetic polymers. Further, there are disclosed in U.S. Pat. No. 4,021,432 the N-methyl derivatives of the above-mentioned compounds.

It was now found that certain 2,2,6,6-tetramethyl-piperidine derivatives in which the above-mentioned known compounds are linked with a group comprising e.g. 3,5-di-t-butyl-4-hydroxyphenyl at 1-position of the piperidine nucleus show a light stabilizing activity, and at the same time, a superior heat-stabilizing activity for synthetic polymers and a processing stability upon heating. The compounds of the invention are hardly volatile and superior also with regard to the compatibility with polymers and the extraction-resistance therefrom and show an excellent toxicological behaviour.

The novel 2,2,6,6-tetramethylpiperidine derivatives of the invention are represented by the following formula (I):

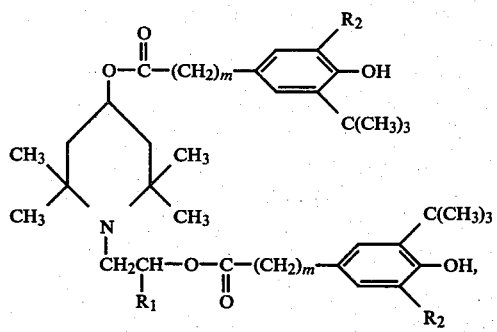

wherein m is 0, 1 or 2, $R_1$ is hydrogen, methyl, ethyl, phenoxymethyl or phenyl, and $R_2$ is $C_1$-$C_8$ alkyl.

The symbols m stand for same or different values, preferably same, and are preferably 2. The symbols $R_2$ preferably stand for the same, and are e.g. methyl, tert.-octyl and above all tert.-butyl.

Preferred compounds of formula I are:
(1) 1-[2-[3-(3,5-di-tert.-butyl-4-hydroxy-phenyl)propionyloxy]-ethyl]-4-[3-(3,5-di-tert.-butyl-4-hydroxy-phenyl)-propionyloxy]-2,2,6,6-tetramethyl-piperidine.
(2) 1-[2-[2-(3,5-di-tert.-butyl-4-hydroxy-phenyl)acetyloxy]-ethyl]-4-[2-(3,5-di-tert.-butyl-4-hydroxy-phenyl)-acetyloxy]-2,2,6,6-tetramethyl-piperidine.
(3) 1-[2-(3,5-di-tert.-butyl-4-hydroxy-benzoyloxy)-ethyl]-4-(3,5-di-tert.-butyl-4-hydroxy-benzoyloxy)-2,2,6,6-tetramethyl-piperidine.
(4) 1-[2-[3-(3,5-di-tert.-butyl-4-hydroxy-phenyl)propionyloxy]-2-methyl-ethyl]-4-[3-(3,5-di-tert.-butyl-4-hydroxy-phenyl)-propionyloxy]-2,2,6,6-tetramethyl-piperidine.
(5) 1-[2-[3-(3,5-di-tert.-butyl-4-hydroxy-phenyl)propionyloxy]-2-ethyl-ethyl]-4-[3-(3,5-di-tert.-butyl-4-hydroxy-phenyl)-propionyloxy]-2,2,6,6-tetramethyl-piperidine.
(6) 1-[2-[3-(3,5-di-tert.-butyl-4-hydroxy-phenyl)propionyloxy]-2-phenyl-ethyl]-4-[3-(3,5-di-tert.-butyl-4-hydroxy-phenyl)-propionyloxy]-2,2,6,6-tetramethyl-piperidine.

Of these, compound (1) is especially preferred.

The 2,2,6,6-tetramethylpiperidine derivatives of formula (I) according to the invention may be prepared by reacting 1-(2-hydroxy-2-$R_1$-ethyl)-2,2,6,6-tetramethyl-4-hydroxy-piperidine with an active derivate of a carboxylic acid (e.g. acid halide, acid anhydride or lower alkyl ester) having the formula

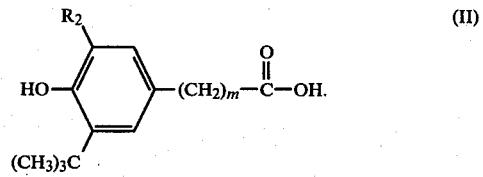

In the above formula II m, $R_1$ and $R_2$ have the meanings defined above.

When the reactive derivative employed is an ester of the acid, the reaction is preferably carried out in the presence of a strong base and of an inert organic solvent.

Examples of suitable solvents are aromatic and aliphatic hydrocarbons such as benzene, toluene, xylene, n-heptane, n-octane and isooctane. Suitable strong bases include, for example: strongly basic alkali metal compounds, such as sodium methoxide, sodium ethoxide, potassium hydroxide or lithium amide; or titanic acid compounds, such as tetraisopropyl titanate or tetrabutyl titanate. It is preferred that the reaction should be carried out with heating, preferably at a temperature from 80°–180° C.

When an acid halide is employed, the reaction is preferably carried out in the presence of an acid-binding agent and of an inert organic solvent. Examples of suitable solvents are: aromatic hydrocarbons, such as benzene, toluene and xylene; halogenated aliphatic hydrocarbons, such as chloroform and trichloroethane; and ethers, such as diethyl ether, tetrahydrofuran and dioxane. Suitable acid-binding agents include: alkali metal hydroxides, such as sodium hydroxide and potassium hydroxide; alkali metal carbonates, such as sodium carbonate and potassium carbonate; and organic bases, such as triethylamine and pyridine. The reaction is usually carried out at a temperature from 0°–130° C.

Where the reactive derivative is an acid anhydride, the reaction is preferably carried out in the presence of an inert organic solvent or in the absence of a solvent but using an excess of acid anhydride. Where a solvent is employed, it is selected from: aromatic hydrocarbons such as benzene, toluene and xylene; and ethers, such as dioxane, tetrahydrofuran and diethylene glycol dimethyl ether. The reaction temperature may preferably be any temperature from ambient to 160° C.

The 2,2,6,6-tetramethylpiperidine derivatives of formula (I) according to the invention can stabilize effectively wide varieties of synthetic polymers.

Synthetic polymers stabilized in this way include:
olefin and diene polymers including homopolymers of olefins and dienes (e.g., low-density, high-density and cross-linked polyethylenes, polypropylene, polyisobutylene, polymethylbutene-1, polymethylpentene-1, polyisoprene and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers commonly known as acrylonitrile/butadiene/styrene or ABS plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide), and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;

polyurethanes and polyureas;
polycarbonates;
polysulphones;
polyamides and copolyamides derived from diamines and dicarboxylic acids and/or from aminocarboxylic acids or the corresponding lactams, including nylon-6, nylon-6,6, nylon-6,10, nylon-11 and nylon-12;

polyesters derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers derived from aldehydes together with phenols, ureas or melamines, e.g. phenol/formaldehyde, urea/formaldehyde and melamine/formaldehyde resins;

alkyd resins e.g. glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof.

The amount of the stabilizers of the invention needed for effective stabilization of organic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but the most effective range will vary with the type of polymer: viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into organic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric composition of the invention may optionally also contain one or more of various additives conventionally used in polymer technology such as the additives listed in British Patent Specification No. 1,401,924, at pages 11 to 13.

The invention is further illustrated by the following Examples, in which all parts are by weight:

EXAMPLE 1

1-[2-{3-(3,5-Di-tert-butyl-4-hydroxyphenyl)propionyloxy}ethyl]-4-{3-(3,5-di-tert-butyl-4-hydroxyphenyl)propionyloxy}-2,2,6,6-tetramethylpiperidine (Compound No. 1)

A mixture of 2.0 g of 1-(2-hydroxyethyl)-4-hydroxy-2,2,6,6-tetramethylpiperidine, 6.4 g of methyl 3-(3,5-di-tert-butyl-4-hydroxyphenyl)propionate and 0.4 g of lithium amide was refluxed in 300 ml of toluene for 8 hours, while removing continuously an azeotropic mixture consisting of toluene and methanol formed in situ. During the reaction, the volume of the reaction mixture was maintained at about 300 ml by adding continuously toluene in an amount corresponding to the azeotropic mixture removed. After completion of the reaction, the reaction mixture was poured into ice-water and the toluene layer was separated and dried over anhydrous magnesium sulfate. After the toluene was evaporated under reduced pressure, the resulting residue was purified by column chromatography through silica gel eluted with benzene, then by recrystallization from n-hexane, giving the desired compound in the form of white crystals melting at 137°–138.5° C.

EXAMPLE 2

Testing of heat-stability

Mixtures of 100 parts of unstabilized polypropylene powder (MFI=15) and 0.25 part of the stabilizing compounds listed in Table 1 were blended and homogenized using a Brabender Plastograph at 200° C. for 10 minutes. The resulting masses were pressed in a laboratory press to form sheets of thickness 2-3 mm. The sheets were heated and pressed using a compression-molding machine at 260° C. for 6 minutes and placed immediately into cold water to form sheets of thickness 0.5 mm. The sheets were cut to form test specimens of size 1×10 cm. Each test specimen was placed in a hot air-circulating thermostat at 150° C. and examined periodically at every 20 hours by bending test to determine the time to embrittlement. Similarly, control test specimens containing a known stabilizer, viz. (A) 4-[3-(3,5-di-tert-butyl)-4-hydroxyphenyl)propionyloxy]-2,2,6,6-tetramethypiperidine, or (B) 4-[3-(3,5-di-tert-butyl-4-hydroxyphenyl)propionyloxy]-1,2,2,6,6-pentamethylpiperidine were prepared and tested for comparison. The results obtained are shown in Table 1.

TABLE 1

| Stabilizer Compound No. | Time to embrittlement |
| --- | --- |
| 1 | 500 hours |
| A | 80 |
| B | 100 |

EXAMPLE 3

Testing of light-stability

The sheets of thickness 0.5 mm obtained in Example 6 were subjected to a pressure of 12 tons by means of a hydraulic press at 260° C. for 6 minutes and then placed immediately into cold water to form films of thickness 0.1 mm. The films were cut to form test specimens of size 50×120 mm. Each test specimen was exposed to light in a Sunshine Weather Meter at a black panel temperature of 63±3° C. and examined periodically to determine the percent elongation at break. The test results were expressed as a ratio of the time required for the test specimen to reach 50% elongation at break when the stabilizer was employed to the time when no stabilizer was employed. The result obtained is shown in Table 2.

TABLE 2

| Stabilizer Compound No. | Ratio |
| --- | --- |
| 1 | 4.5 |

EXAMPLE 4

Testing of heat-stability upon processing

Mixtures were made from 38 g of unstabilized polypropylene powder and 38 mg of the stabilizer compounds listed in Table 3 (0.1% by weight based on the polymer), blended and homogenized using a Brabender Plastograph at 200° C. for 10 minutes at 30 rpm/min. During the mixtures were hot, they were rolled to form plates of thickness 1-2 mm, which were cut finely to form test specimens. The melt flow index (MFI) of the test specimens were determined under the operation condition L and operation procedures B (automatic timing determination) as prescribed for in ASTMD-1238-73. Control test specimens containing no stabilizer or stabilizer (A) or (B) employed in Example 2 were prepared and tested for comparison. The results obtained are shown in Table 3.

TABLE 3

| Stabilizer Compound No. | MFI |
| --- | --- |
| 1 | 5.8 |
| A | 12.9 |
| B | 29.9 |
| none | 164 |

EXAMPLE 5

Testing of stabilizer evaporation 6 to 8 mg of the stabilizer compound listed in Table 4 was placed on a thermobalance and heated under conditions of 50 ml/min. of air flow and 5° C./min. of temperature elevation. The percentage of remained stabilizer was measured at 250° C. and 300° C. The results are obtained are shown in Table 4.

TABLE 4

| Stabiliser Compound No. | Remaining amount (%) | |
| --- | --- | --- |
|  | 250° C. | 300° C. |
| 1 | 100.0 | 95.8 |

I claim:

1. 2,2,6,6-Tetramethylpiperidine derivatives having the formula

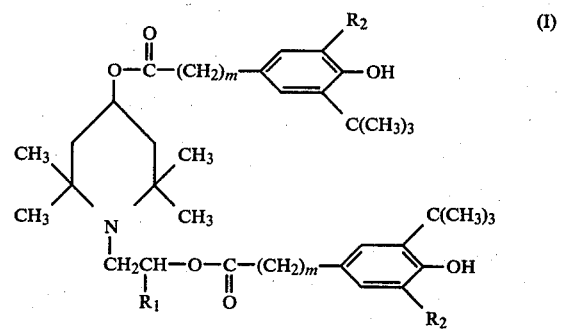

wherein m is 0, 1 or 2, $R_1$ is hydrogen, methyl, ethyl, phenoxymethyl or phenyl, and $R_2$ is $C_1$-$C_8$ alkyl.

2. A compound as claimed in claim 1 being 1-{2-[3-(3,5-di-tert.-butyl-4-hydroxy-phenyl)-propionyloxy]-ethyl}-4-[3-(3,5-di-tert.-butyl-4-hydroxy-phenyl)-propionyloxy]-2,2,6,6-tetramethyl-piperidine.

3. Stabilized synthetic polymer compositions containing a 2,2,6,6-tetramethylpiperidine derivative as defined in claim 1 or 2.

* * * * *